United States Patent
Spalding et al.

(10) Patent No.: US 9,863,813 B2
(45) Date of Patent: Jan. 9, 2018

(54) FLAME SENSOR

(75) Inventors: Michael Charles Spalding, Hudson, OH (US); Donald Albert Schneider, Lakewood, OH (US); Jiyuan Liu, Solon, OH (US); Frederick Louis Glesius, Brecksville, OH (US); Jeffrey Louis Johanning, Hudson, OH (US); Leo Raymond Lombardo, Highland Hts., OH (US); Fred Yu-Feng Chou, Stow, OH (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1493 days.

(21) Appl. No.: 13/445,953

(22) Filed: Apr. 13, 2012

(65) Prior Publication Data

US 2013/0273483 A1    Oct. 17, 2013

(51) Int. Cl.
| | |
|---|---|
| *G01J 1/42* | (2006.01) |
| *G01J 5/08* | (2006.01) |
| *G01J 5/00* | (2006.01) |
| *G01J 5/04* | (2006.01) |
| *G01J 5/20* | (2006.01) |
| *G01N 21/33* | (2006.01) |

(52) U.S. Cl.
CPC .......... *G01J 5/0821* (2013.01); *G01J 5/0014* (2013.01); *G01J 5/042* (2013.01); *G01J 5/0806* (2013.01); *G01J 5/0818* (2013.01); *G01J 5/20* (2013.01); *G01N 21/33* (2013.01); *G01N 2201/021* (2013.01); *G01N 2201/084* (2013.01)

(58) Field of Classification Search
CPC ...... G01J 5/0014; G01J 5/0806; G01J 5/0821; G01J 5/0862; G01J 1/0425; G01J 3/0218; G01J 5/042; G01J 5/0818; G01J 5/20; G01N 21/33; G01N 2201/021; G01N 2201/084

USPC .......................................................... 250/372
See application file for complete search history.

(56) References Cited

U.S. PATENT DOCUMENTS

| | | | | |
|---|---|---|---|---|
| 4,616,137 A | * | 10/1986 | Goff ........................ | F23N 5/082 250/227.23 |
| 4,855,718 A | * | 8/1989 | Cholin .................... | F23N 5/082 250/554 |
| 5,190,364 A | * | 3/1993 | Imoto .................. | G02B 6/2856 385/15 |
| 5,317,165 A | * | 5/1994 | Montagna ............... | F23N 5/082 250/227.23 |

(Continued)

OTHER PUBLICATIONS

Corresponding Chinese application, application No.: 201310125964.4, Chinese Office action dated May 3, 2017, 9 pages.

*Primary Examiner* — Taeho Jo
(74) *Attorney, Agent, or Firm* — Cooper Legal Group, LLC

(57) ABSTRACT

A flame sensor apparatus is provided including a sensor for sensing specific characteristics of a flame within a combustion chamber. The sensor includes a silicon carbide photodiode, and the sensor is spaced a distance from the combustion chamber. In addition, a fiber optic cable assembly extends between the sensor and the combustion chamber. The fiber optic cable can convey the specific characteristics of the flame from the combustion chamber to the sensor. The fiber optic cable assembly is included as part of a sealed array filled with an inert gas. In addition, a method of sensing specific characteristics of a flame is also provided.

20 Claims, 5 Drawing Sheets

(56) References Cited

U.S. PATENT DOCUMENTS

| | | | |
|---|---|---|---|
| 5,515,681 A * | 5/1996 | DeFreitas | F23Q 13/00 60/39.821 |
| 5,659,133 A * | 8/1997 | Sims | G01M 15/10 313/323 |
| 5,670,784 A * | 9/1997 | Cusack | G01J 5/0014 250/370.01 |
| 5,828,797 A * | 10/1998 | Minott | F01D 17/02 250/227.23 |
| 5,929,450 A * | 7/1999 | Glasheen | G01J 5/0014 250/339.15 |
| 6,013,919 A * | 1/2000 | Schneider | F23N 5/082 250/554 |
| 6,071,114 A * | 6/2000 | Cusack | F01D 17/02 340/578 |
| 6,175,676 B1 * | 1/2001 | Sharan | C21O 5/30 250/316.1 |
| 6,422,745 B1 * | 7/2002 | Glasheen | G01J 5/0014 374/121 |
| 6,700,495 B2 | 3/2004 | mindermann et al. | |
| 8,485,040 B2 * | 7/2013 | Petersen | G01L 19/0645 73/706 |
| 2003/0056550 A1 * | 3/2003 | Tanaka | C03B 37/0122 65/428 |
| 2004/0033457 A1 * | 2/2004 | Zhang | F23N 5/082 431/79 |
| 2005/0121614 A1 * | 6/2005 | Stuttard | G01N 21/3504 250/343 |
| 2005/0252246 A1 * | 11/2005 | Shirley | C03B 37/02718 65/391 |
| 2006/0263074 A1 * | 11/2006 | Xing | A61F 7/007 392/407 |
| 2007/0207423 A1 * | 9/2007 | Chase | F23N 5/082 431/79 |
| 2009/0003785 A1 * | 1/2009 | Parris | G02B 6/4494 385/123 |
| 2009/0060246 A1 * | 3/2009 | Baliga | H04R 19/005 381/354 |
| 2009/0229811 A1 * | 9/2009 | Schmitt | G01J 5/0014 165/287 |
| 2010/0103424 A1 * | 4/2010 | Davis, Jr. | F23N 5/082 356/402 |
| 2010/0151397 A1 * | 6/2010 | Farrell | F23N 5/08 431/4 |
| 2010/0318274 A1 * | 12/2010 | Krull | F23M 11/00 701/100 |
| 2011/0008737 A1 * | 1/2011 | McManus | F23N 1/022 431/12 |
| 2011/0232296 A1 * | 9/2011 | Frederick | F23D 14/725 60/776 |
| 2012/0164589 A1 * | 6/2012 | Wehe | F02D 35/022 431/253 |
| 2013/0031957 A1 * | 2/2013 | Shaw | G08B 17/00 73/28.01 |

* cited by examiner

FLAME SENSOR

BACKGROUND OF THE INVENTION

Field of the Invention

The invention relates to a flame sensor and, more particularly, to a fiber optic flame sensor for sensing specific characteristics of a flame in a combustion chamber.

Discussion of Prior Art

Within an oil or gas fueled turbine, fuel is fed into a combustion chamber within which an ignition flame is present. If the flame becomes extinguished, commonly referred to as a flame-out condition, it is a concern that fuel may continue to be fed into the hot combustion chamber without appropriate ignition. Damage to the turbine can occur if the fuel is inappropriately ignited (e.g., ignition caused by something other than the ignition flame in view of the absence of the flame). Consequently, if the ignition flame is extinguished within the combustion chamber, it is critical that the fuel feed into the combustion chamber is quickly terminated and thus limit un-combusted fuel build up.

A flame sensor is generally used for detecting the presence or absence of an ignition flame within a combustion chamber of a gas turbine. Also, flame sensing electronics are commonly associated with the flame sensor within the turbine arrangement. The flame sensing electronics may be temperature sensitive. Due to the relatively hot temperatures in and near the combustion chamber, water cooling is often used to cool the temperature sensitive flame sensing electronics. However, water may occasionally leak and, if sprayed on the relatively hot housing of the turbine, may cause the turbine housing to contract, causing damage to the turbine. Accordingly, it would be useful to provide a flame sensor that eliminates the need for water cooling and which circuitry is not affected by the relatively high temperature near the combustion process/chamber.

BRIEF DESCRIPTION OF THE INVENTION

The following summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

In accordance with one aspect, the present invention provides a flame sensor apparatus comprising a sensor for sensing specific characteristics of a flame within a combustion chamber, the sensor including a silicon carbide photodiode, wherein the sensor is spaced a distance from the combustion chamber, and a fiber optic cable assembly extending between the sensor and the combustion chamber, the fiber optic cable assembly being configured to convey the characteristics of the flame from the combustion chamber to the sensor, wherein the fiber optic cable assembly is included as part of a sealed array filled with an inert gas.

In accordance with another aspect, the present invention provides a flame sensor apparatus comprising a sensor for sensing specific characteristics of a flame within a combustion chamber, the sensor including a silicon carbide photodiode, a probe assembly spaced a distance away from the combustion chamber, the probe assembly configured to receive characteristics of the flame from the combustion chamber, and a fiber optic cable assembly extending between the sensor and the probe assembly, the fiber optic cable assembly being configured to convey the characteristics of the flame from the probe assembly to the sensor.

In accordance with another aspect, the present invention provides a method of sensing specific characteristics of a flame within a combustion chamber, comprising the steps of receiving electromagnetic radiation energy from the flame by a fiber optic cable assembly, conveying the electromagnetic radiation energy from the fiber optic cable assembly to a sensor spaced a distance away from the flame and outside of the combustion chamber, focusing the electromagnetic radiation energy from the fiber optic cable assembly onto a silicon carbide photodiode within the sensor, and sensing the characteristics of the flame with the silicon carbide photodiode based on the electromagnetic radiation energy.

BRIEF DESCRIPTION OF THE DRAWINGS

The foregoing and other aspects of the invention will become apparent to those skilled in the art to which the invention relates upon reading the following description with reference to the accompanying drawings, in which.

DETAILED DESCRIPTION OF THE INVENTION

Figure 1:
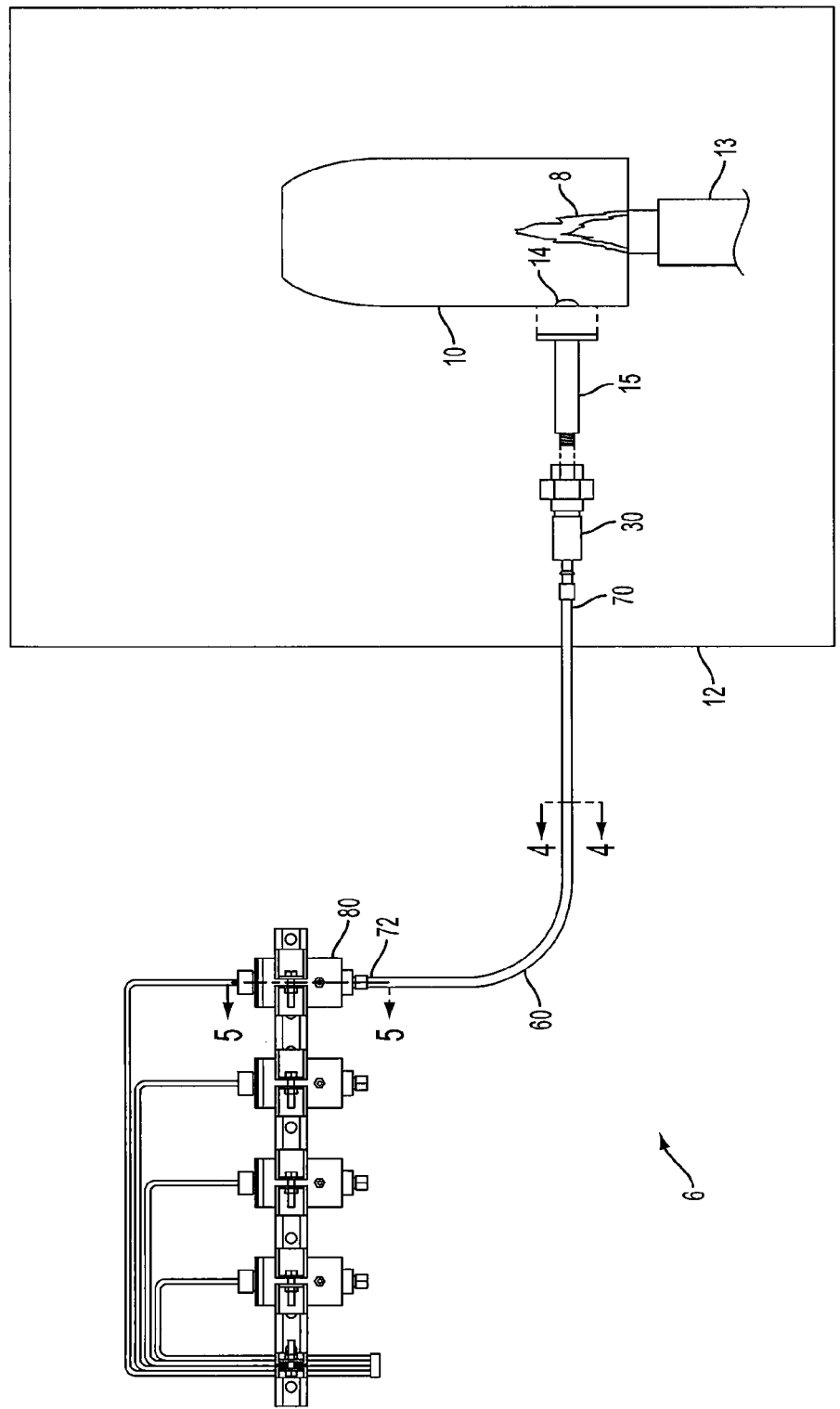
FIG. 1 is a partially exploded, schematized cross-section view of an example flame sensor apparatus in accordance with at least one aspect of the present invention.

Example embodiments that incorporate one or more aspects of the invention are described and illustrated in the drawings. These illustrated examples are not intended to be a limitation on the invention. For example, one or more aspects of the invention can be utilized in other embodiments and even other types of devices. Moreover, certain terminology is used herein for convenience only and is not to be taken as a limitation on the invention. Still further, in the drawings, the same reference numerals are employed for designating the same elements.

FIG. 1 schematically illustrates an example flame sensor apparatus 6 for monitoring specific characteristics of a flame 8. In short summary, the flame 8 is located within a combustion chamber 10 of a turbine compartment 12 and emits electromagnetic radiation energy. A sight tube 15 having a hollow internal bore can be attached to the combustion chamber 10. A probe assembly 30 can receive the electromagnetic radiation energy from the flame 8 through the sight tube 15. The electromagnetic radiation energy can then pass from the probe assembly 30, through a fiber optic cable assembly 60, and to a sensor 80, whereupon the sensor 80 can sense the flame's specific characteristics, such as the presence or absence of the flame. In accordance with an aspect of the present invention, the sensor 80 can be positioned a distance away from the combustion chamber 10 and the turbine compartment 12 such that the sensor 80 can monitor the flame's specific characteristics while being located in a relatively cooler environment.

Turning to the specific example shown in FIG. 1, the turbine compartment 12 can include a rotating turbine blade (not shown) powered by fuel combustion within the combustion chamber 10. The turbine compartment 12 is generically/schematically shown in FIG. 1 to convey the concept that the turbine compartment 12 can have varied, different structures and/or could be used in varied, different applications. For example, the turbine compartment 12 could be constructed/configured for oil and gas combustion turbines and used in applications such as for aircraft propulsion, marine propulsion, land-based power generation, or the like. As such, it is to be appreciated that the turbine compartment 12 in FIG. 1 is not intended to be limiting on further examples.

The combustion chamber 10 can be positioned within the turbine compartment 12. The combustion chamber 10 can define a substantially hollow internal area. It is to be understood that the combustion chamber 10 is generically/schematically represented in FIG. 1, and is not intended to be limiting on further examples. For instance, the generic representation of the combustion chamber 10 is intended to convey the concept that the combustion chamber 10 can represent a number of different constructions, some of which may be generally known. Similarly, the combustion chamber 10 described herein and as in association with the turbine compartment 12 discussed above may be incorporated into a number of different applications.

Fuel is within the combustion chamber 10 to produce a relatively high-pressure and high-velocity gas. A fuel nozzle 13 can be provided that delivers fuel into the combustion chamber 10. It is to be understood that the term "fuel" can encompass air, fuel, a mixture of both, and/or nearly any type of combustible material. The fuel nozzle 13 can cooperate with an opening, orifice, or the like in the combustion chamber 10 such that the fuel nozzle 13 can deliver the fuel from an exterior location into the combustion chamber 10. As such, the fuel nozzle 13 can deliver the fuel into the combustion chamber, whereupon the fuel can be ignited with the flame 8. Again, the fuel nozzle 13 is generically/schematically represented in the shown example, and may include any number of fuel nozzle constructions that may be known. Further, the fuel nozzle 13 could be positioned at a number of locations within the combustion chamber 10, and is not limited to the location shown in FIG. 1.

An opening 14 can be provided in an outer wall of the combustion chamber 10. The opening 14 (shown generically in FIG. 1 and in phantom in FIG. 2, as opening 14 is not normally visible in such a view), can extend completely through the outer wall. As such, an interior of the combustion chamber 10 can be optically exposed to a location that is exterior from the combustion chamber 10. The opening 14 can be positioned in near proximity to the flame 8, such that the opening 14 defines an optical path through the opening 14 and towards the flame 8. The temperature adjacent the opening 14 can, in one example, be about 454° C., though a wide range of temperatures are contemplated. It is to be understood that the opening 14 is not limited to the location shown in FIG. 1, and could be positioned at a number of different locations on the combustion chamber 10. For instance, the opening 14 could be positioned closer or farther from the fuel nozzle 13. Similarly, the opening 14 could be larger or smaller, or could comprise more than one opening.

The sight tube 15 is located on the optical path from the flame 8 and through the opening 14. FIG. 1 depicts an exploded view of the sight tube 15 for illustrative purposes to show the structural relationship between the sight tube 15 and the opening 14. It is to be understood, however, that in operation, the sight tube 15 and combustion chamber 10 are in a fully assembled state with the sight tube attached to the combustion chamber 10. The sight tube 15 can be attached to the combustion chamber 10 in any number of ways, such as by mechanical fasteners, welding, adhesives, or the like.

Figure 2:
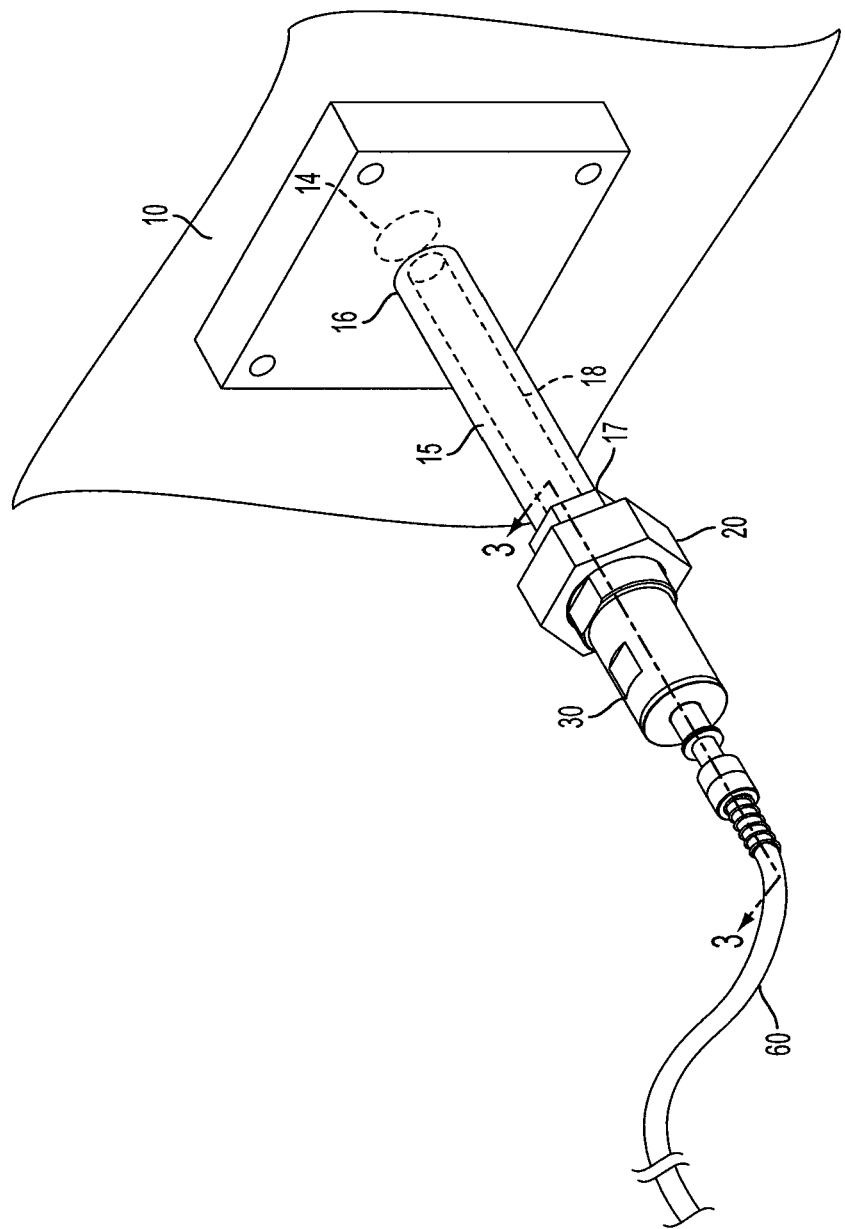
FIG. 2 is a perspective view of an example probe assembly including an example sight tube in accordance with an aspect of the present invention.

Referring now to FIG. 2, the sight tube 15 can now be explained in more detail. The sight tube 15 includes an elongated, substantially hollow cylindrical structure that extends between a first end portion 16 and an opposing second end portion 17. The sight tube 15 can include a variety of sizes and shapes, though in one example, the sight tube 15 can be approximately 152.4 millimeters (6 inches) in total length. The sight tube 15 can define an internal bore 18 that is substantially hollow and extends longitudinally between the first end portion 16 and the second end portion 17. The internal bore 18 of the sight tube 15 is shown in phantom in FIG. 2, as the internal bore 18 is not normally visible in such a view. The internal bore 18 is not limited to the size and shape shown in FIG. 2, and, in other examples, could include a larger or smaller cross-sectional diameter. Accordingly, it is to be understood that the sight tube 15 shown in FIG. 2 is merely one example of a sight tube 15, as any number of constructions are envisioned.

The sight tube 15 can be attached to the opening 14, such that an interior of the combustion chamber 10 is optically exposed to the internal bore 18 of the sight tube 15. In operation, the internal bore 18 of the sight tube 15 can be aligned with the opening 14, such that the sight tube 15 defines an optical path through the internal bore 18, through the opening 14, and into the interior area of the combustion chamber 10. The sight tube 15 can be aligned with the flame 8, thus allowing for electromagnetic radiation energy from the flame to propagate through the internal bore 18 of the sight tube 15.

Figure 3:
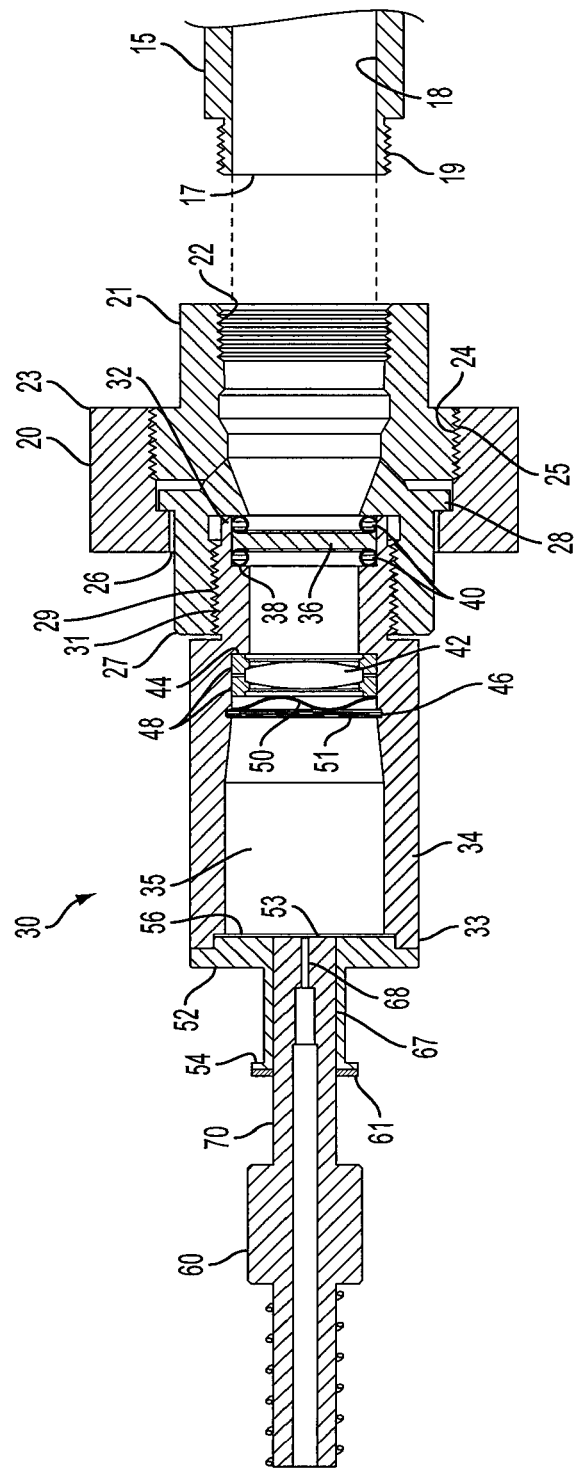
FIG. 3 is a partially exploded sectional view of the example probe assembly along line 3-3 of FIG. 2.

Referring now to FIG. 3, a cross-sectional view along line 3-3 of FIG. 2 is shown, depicting the second end portion 17 of the sight tube 15. The sight tube 15 can include an attachment structure, such as a threaded portion or a screw thread 19, positioned at the second end portion 17. It is to be understood that the sight tube 15 could include any number of attachment structures, and is not limited to the screw thread 19 shown in FIG. 3. In one example, the screw thread 19 can be formed at an outer surface of the second end portion 17 of the sight tube 15. The screw thread 19 can include an external male thread formed at an outer surface of the sight tube 15. In one instance, the screw thread 19 can include a ¾" NPT pipe thread. Of course, the screw thread 19 could include a number of different constructions and is not limited to the structure shown. For instance, the screw thread 19 could extend along a longer or shorter axial length of the sight tube 15, could have larger or smaller threads, etc.

Referring still to FIG. 3, the sight tube 15 can be attached at the second end portion 17 to a union nut 20. It is to be understood that FIG. 3 depicts an exploded view of the sight tube 15 for illustrative purposes. However, in operation, the sight tube 15 is in a fully assembled state and is attached to the union nut 20. Specifically, the sight tube 15 can be attached to a first nut end portion 21 of the union nut 20. The first nut end portion 21 can define a rounded, cylindrically shaped structure with a hollow internal bore extending between a first end and a second end. The first nut end portion 21 can include an attachment structure, such as a threaded portion 22. The threaded portion 22, which may include a female screw thread, or the like, can be formed at an inner surface of the internal bore of the first nut end portion 21. The threaded portion 22 can extend at least partially along the length of the first nut end portion 21, though the threaded portion 22 could extend a longer or shorter distance than shown in the example.

The screw thread 19 of the sight tube 15 can be sized and shaped to mate with the threaded portion 22 of the first nut end portion 21. Specifically, a diameter of the second end portion 17 of the sight tube 15 can be slightly smaller than an internal bore diameter of the first nut end portion 21. As such, the internal bore of the first nut end portion 21 can receive the second end portion 17 of the sight tube 15. Further, the screw thread 19 of the sight tube 15 can engage and mate with the threaded portion 22. As such, the first nut end portion 21 can be removably attached in a threaded manner to the sight tube 15. Of course, it is to be understood that the attachment of the first nut end portion 21 and sight tube 15 described herein and shown in FIG. 3 is merely one possible example of attachment. For instance, in another example, the sight tube 15 could include a female threaded portion while the first nut end portion 21 can include a male threaded portion, such that the first nut end portion 21 can be inserted into the sight tube 15. In further examples, a variety of attachment means are envisioned for attaching the first nut end portion 21 and the sight tube 15 including, but not limited to, welding, mechanical fasteners, adhesives, or the like.

The union nut 20 can now be described in more detail. The first nut end portion 21 can further include a second attachment structure positioned at an opposite end from the threaded portion 22. In one example, the first nut end portion 21 could include an external threaded portion 24. The external threaded portion 24 can be formed on an outer surface of the first nut end portion 21. The external threaded portion 24 can extend at least partially along a length of the first nut end portion 21.

Referring still to FIG. 3, the union nut 20 can further include a central nut portion 23. The central nut portion 23 can include a hollow internal bore extending between opposing end portions. The internal bore of the central nut portion 23 can include a diameter that is slightly larger than an outer diameter at the threaded portion 22 of the first nut end portion 21. The central nut portion 23 can include an internal threaded portion 25 positioned adjacent an end of the central nut portion 23. The internal threaded portion 25 can extend at least partially along a length of the central nut portion 23 and can be formed within an internal surface or wall of the central nut portion 23.

The central nut portion 23 and the first nut end portion 21 can be attached. For instance, the internal threaded portion 25 of the central nut portion 23 can be sized and shaped to mate with the external threaded portion 24 of the first nut end portion 21. Specifically, a diameter of the internal bore of the central nut portion 23 can be slightly larger than an outer diameter of the first nut end portion 21 at the external threaded portion 24. As such, the internal bore of the central nut portion 23 can receive the first nut end portion 21. The external threaded portion 24 of the first nut end portion 21 can engage and mate with the internal threaded portion 25. Accordingly, the first nut end portion 21 can be removably attached to the central nut portion 23. It is to be understood that the attachment of the first nut end portion 21 and the central nut portion 23 described herein is merely one possible example of an attachment means. Accordingly, any number of attachment means and structures for attaching the first nut end portion 21 and central nut portion 23, including mechanical fasteners, welding, adhesives, or the like.

Referring still to FIG. 3, the central nut portion 23 can further include an inward protrusion 26 that projects inwardly from an outer surface of the central nut portion 23.

The inward protrusion 26 can be positioned at an opposite end of the central nut portion 23 from the end having the internal threaded portion 25. The inward protrusion 26 is longitudinally spaced a distance apart from the internal threaded portion 25, such that a gap exists between the inward protrusion 26 and the internal threaded portion 25. The inward protrusion 26 can include an inner diameter that is smaller than the diameter of the remaining portion of the central nut portion 23.

The union nut 20 can further include a second nut end portion 27. The second nut end portion 27 can define a substantially cylindrically shaped structure having a hollow internal bore extending between opposing end portions. The second nut end portion 27 can include a nut projection 28 that projects radially outwardly from an outer surface of the second nut end portion 27. The nut projection 28 can have an outer diameter that is slightly smaller than an inner diameter of the central nut portion 23. As such, the nut projection 28 can be positioned within the central nut portion 23 while the remainder of the second nut end portion 27 can project outwardly from the central nut portion 23 in a direction away from the first nut end portion 21. The nut projection 28 can be positioned axially between the first nut end portion 21 on one side and the inward protrusion 26 of the central nut portion 23 on a second side. As such, the nut projection 28 can be limited from moving axially by the first nut end portion 21 and the inward protrusion 26. Moreover, the nut projection 28 can be limited from moving radially by the central nut portion 23. Accordingly, the second nut end portion 27 can be limited from moving radially or axially with respect to the central nut portion 23 and the first nut end portion 21.

The second nut end portion 27 can be movably attached to the central nut portion 23. Accordingly, while remaining sandwiched between the inward protrusion 26 and the first nut end portion 21, the nut projection 28 can rotate with respect to the central nut portion 23. More specifically, the central nut portion 23 and the first nut end portion 21 can rotate with respect to nut projection 28. This rotational movement can allow the central nut portion 23 and the first nut end portion 21 to be attached in a threaded manner to the sight tube 15 by rotation while the second nut end portion 27 remains relatively motionless.

The second nut end portion 27 can further include a nut groove 29. The nut groove 29 can be positioned with an internal wall of the second nut end portion 27. The nut groove 29 can extend circumferentially around the internal wall of the second nut end portion 27 and can extend at least partially along the length of the second nut end portion 27. In one example, the nut groove 29 can include an internal threaded portion. The internal threaded portion can extend circumferentially around an internal bore of the nut groove 29. The internal threaded portion can extend at least partially along a length of the nut groove from one end towards an opposing end. It is to be understood, however, that the second nut end portion 27 is not limited to the size and shape in the example, and could be larger or smaller in diameter, or the internal threaded portion could extend along a longer or shorter distance than shown in the example.

Referring still to FIG. 3, the union nut 20 can be attached to the probe assembly 30. The probe assembly 30 can include a probe projection 31 formed at an outer surface of the probe assembly 30. The probe projection 31 can include a threaded portion that extends radially outwardly from the outer surface of the probe assembly 30. The threaded portion can extend circumferentially around an outer surface of the probe projection 31. In operation, the probe projection 31 can be received within the nut groove 29 in a threading manner to attach the probe assembly 30 to the union nut 20. The nut groove 29 can be sized to match the probe projection 31, such that the nut groove 29 can have a slightly larger diameter than the probe projection 31. As such, the internal threaded portion of the nut groove 29 can receive the threaded portion of the probe projection 31 in a threaded manner, such that the probe projection 31 is limited from either or both axial and radial movement.

It is to be understood that the attachment between the probe assembly 30 and the union nut 20 shown in FIG. 3 is merely one possible example of attachment, and is not intended to be limiting on further aspects of the invention. In other examples, the probe assembly 30 could be attached to the union nut 20 by welding, mechanical fasteners, snap fit means, or the like. In these examples, the probe assembly 30 may be provided without the probe projection 31 while the union nut 20 could be provided without the nut groove 29. In other examples, the probe assembly 30 could be attached directly to the sight tube 15, such that the union nut 20 may not be provided. In this example, the probe assembly 30 could be attached to the sight tube 15 in any number of ways, including, but not limited to, welding, mechanical fasteners, threading attachment, snap fit means, or the like.

Referring still to FIG. 3, the probe assembly 30 can now be described in more detail. Due to the attachment of the probe assembly 30 to the sight tube 15 via the union nut 20, the probe assembly 30 is spaced a distance away from the combustion chamber 10. For instance, the probe assembly 30 could be spaced about 152.4 millimeters (6 inches) away from the combustion chamber 10, though larger or smaller distances are contemplated. By being spaced away from the combustion chamber 10, the probe assembly 30 can be subjected to relatively lower temperatures than the sight tube 15. For instance, the temperature at a first probe end portion 32 could be in a range of about −55° C. to about 371° C. However, the temperature can be lower at downstream locations of the probe assembly 30, such as in the range of about −55° C. to about 200° C.

The probe assembly 30 can include a probe body 34 extending along a substantially longitudinal axis. The probe body 34 can be constructed of a number of materials, including relatively high temperature materials that can withstand the aforementioned temperatures associated with the combustion process. In further examples, the probe body 34 could be constructed of materials that can withstand even higher temperatures than described herein. The probe body 34 can be formed of any number of metal-like materials that may be resistant to corrosion. In some examples, the probe body 34 can include 304 stainless steel, 316 stainless steel, or the like.

The probe body 34 defines an internal probe chamber 35 that is substantially hollow and extends axially along the length of the probe body 34 between the first probe end portion 32 and the second probe end portion 33. The probe body 34 extends along a longitudinal axis that is substantially coaxial with a longitudinal axis of the sight tube 15 and the union nut 20. As such, the internal probe chamber 35 of the probe body 34 is substantially coaxial with the internal bore 18 of the sight tube 15 and the opening 14. Accordingly, an optical path can extend through the probe body 34, through the sight tube 15, and towards the flame 8. As such, the electromagnetic radiation energy can propagate from the flame 8, through the opening 14 and sight tube 15, and into the probe body 34 of the probe assembly 30.

The internal structure of the probe assembly 30 can now be described beginning near the first probe end portion 32. The probe assembly 30 can include a window 36 positioned within the internal probe chamber 35 of the probe body 34. The window 36 can be positioned adjacent the first probe end portion 32 of the probe body 34. The window 36 can be oriented substantially perpendicularly with respect to the longitudinal axis of the probe body 34, such that the window 36 extends radially across the internal probe chamber 35. The window 36 can include a variety of different materials, but, in one example, includes a sapphire material.

The window 36 can be positioned within a window groove 38 formed in an internal surface of the internal probe chamber 35. The window groove 38 can extend circumferentially around the internal surface of the internal probe chamber 35. The window groove 38 can have a larger diameter than neighboring portions of the internal probe chamber 35. Both the window groove 38 and the window 36 can include a substantially circular shape. As such, the window 36 can have a diameter that is slightly smaller than the window groove 38, such that the window 36 can closely abut the window groove 38. It is to be understood that the window groove 38 and the window 36 are not limited to the size and shape in the example. Rather, the window groove 38 could include a non-circular shape, such as a spherical shape, rectangular shape, or the like. Similarly, the window 36 could also include a shape that matches the shape of the window groove 38, such that the window 36 could also be non-circular. In further examples, the probe assembly 30 may not include the window groove 38 and, instead, could include the window 36 attached within the internal probe chamber 35 with nearly any type of attachment structure, including mechanical fasteners, adhesives, brazing, or the like.

The window 36 can be positioned between one or more shock absorbing structures. In the shown example, the shock absorbing structures can include a pair of sealing washers 40, though, a variety of shock absorbing structures are envisioned. The window 36 can be positioned between the sealing washers 40. The sealing washers 40 can include a circularly shaped structure having an internal bore extending axially through a center of the sealing washers 40. The sealing washers 40 can be formed of a number of different materials, including metal-like materials, elastomer-like materials, etc. In further examples, the sealing washers 40 could include materials that can withstand the relatively high temperature that the probe assembly 30 is subjected to.

The sealing washers 40 can include a diameter that is slightly smaller than a diameter of the window groove 38, such that the sealing washers 40 can be received within the window groove 38 and be limited from moving axially along the length of the probe body 34. In one example, to further limit movement, the sealing washers 40 could be brazed to either or both of the window 36 and the window groove 38. Accordingly, the window 36 can be limited from moving axially along the length of the probe assembly by the sealing washers 40. Moreover, the sealing washers 40 are internally energized and form a seal with the window 36 and the probe body 34. In this example, the window 36 and sealing washers 40 form a seal that forms a pressure barrier. For instance, the window 36 and sealing washers 40 can withstand gas temperatures of a relatively high temperature, such as in the range of about 850° F., and pressures reaching at least 300 lbs/in$^2$. However, it is to be understood that a variety of different windows 36 and sealing washers 40 could be implemented in the probe assembly 30 that can withstand higher or lower temperatures and pressures. In one example, however, the window 36 and sealing washers 40 can, together, function as a protective sealing barrier that separates an upstream volume (i.e., from the combustion chamber 10, through the sight tube 15 and union nut 20, and to the window 36) from a downstream volume (i.e., from the window 36 towards the second probe end portion 33). Accordingly, in this example, the window 36 and internally energized sealing washers 40 can function to shield and/or protect the downstream volume from the relatively high temperature and pressure in the combustion chamber 10.

Further downstream from the window 36, the probe assembly 30 can include a probe lens 42. The probe lens 42 can be positioned downstream from the window 36. The probe lens 42 can be positioned between the window 36 and the second probe end portion 33 of the probe body 34. The probe lens 42 can be located within the internal probe chamber 35 of the probe body 34. The probe lens 42 can be oriented substantially perpendicularly with respect to the longitudinal axis of the probe body 34, such that the probe lens 42 extends radially across the internal probe chamber 35. The probe lens 42 can include a number of different types of lenses, such as a biconvex lens, plano-convex lens, or the like. Furthermore, the probe lens 42 can include a fused silica lens. The probe lens 42 can be formed of a number of different materials, however, that can withstand the relatively high temperature, pressure, and vibratory environment that the probe assembly 30 can encounter. As will be discussed in more detail below, the probe lens 42 can focus the electromagnetic radiation energy from the flame towards the second probe end portion 33.

The probe lens 42 can be supported by one or more lens washers 48. The shown example of FIG. 3 includes two metal washers, however, it is to be understood, more or fewer washers are envisioned. The lens washers 48 can be positioned on opposing sides of the probe lens 42, such that the probe lens 42 is substantially sandwiched between the lens washers 48. The lens washers 48 can have a substantially circular shape with an internal bore extending through a center. The lens washers 48 can be formed of a number of different materials, including metal-like materials. In one example, one of the lens washers 48 can be positioned upstream from the probe lens 42 between the probe lens 42 on one side and an internal ledge 44 on an opposing side. The lens washers 48 can, in one example, be brazed and/or welded to the probe body 34, such that the probe lens 42 is limited from moving axially along the length of the probe body 34.

The probe assembly 30 can further include a wave spring 50. The wave spring 50 can support the probe lens 42. The wave spring 50 can be positioned adjacent one of the lens washers 48 on a downstream side of the probe lens 42. The wave spring 50 can allow for the probe lens 42 to move axially a limited distance to accommodate for the relatively high vibration endured near the combustion chamber 10. The wave spring 50 is not limited to the size, shape, and location of the example shown in FIG. 3. Rather, the wave spring 50 could instead be positioned upstream and in front of the probe lens 42, such that the wave spring 50 is positioned between the probe lens 42 and the window 36.

The probe assembly 30 can further include a retaining ring 51. The retaining ring can be received within an indentation 46 formed within an interior surface of the probe body 34. Of course, the retaining ring 51 could be secured in other ways within the probe assembly 30, such as with mechanical fasteners, adhesives, or the like. The retaining ring 51 can be positioned downstream and adjacent the wave spring 50. As such, retaining ring 51 can limit axial movement of the wave spring 50 in a direction away from the probe lens 42. Of course, it is to be appreciated that the retaining ring 51 shown herein includes merely one possible example of a retaining ring 51, as any number of embodiments and structures are envisioned.

Further downstream from the probe lens 42, the probe assembly 30 can include an end wall 52 positioned at a downstream end of the probe body 34 at the second probe end portion 33. The end wall 52 can extend radially across the probe body 34 and can include a second end portion opening 53 extending through the end wall 52. The end wall 52 could be attached to the probe body 34 in any number of ways. In one example, the end wall 52 could be welded to the probe body 34. However, other attachment means are envisioned, such as mechanical fasteners, adhesives, or the like. In further examples, the end wall 52 could be integrally formed with the probe body 34, such that the probe body 34 and end wall 52 are a single piece structure. The end wall 52 can include an end wall surface 56 that defines a downstream end of the internal probe chamber 35.

The end wall 52 can further include a flange portion 54. The flange portion 54 can project outwardly in a direction away from the second probe end portion 33. The flange portion 54 can define an internal bore extending therethrough between opposing first and second ends. As such, the internal bore extending through the flange portion 54 can be coaxial with the second end portion opening 53.

As will be described in more detail below, the second end portion opening 53 can be sized to receive an end of the fiber optic cable assembly 60. As such, an end of the fiber optic cable assembly 60 can protrude into the probe body 34 through the second end portion opening 53. In operation, electromagnetic radiation energy from the flame 8 can be focused by the probe lens 42 onto the end of the fiber optic cable assembly 60.

The operation of the probe assembly 30 can now be briefly described. Electromagnetic radiation energy can be transferred from the flame 8 into the sight tube 15 before entering the probe assembly 30. The electromagnetic radiation energy can then pass through the window 36 and through the probe lens 42. The probe lens 42 can focus the electromagnetic radiation energy onto the end of the fiber optic cable assembly 60 located at the second end portion opening 53. In one example, the probe lens 42 can focus the electromagnetic radiation energy onto the fiber optic cable assembly 60 on a spot that has about a 2 millimeter diameter. However, it is to be understood that the spot size is not limited to 2 millimeters, and could be larger or smaller, such as by being +/−0.08 millimeters larger or smaller than 2 millimeters (range of from about 1.92 mm to about 2.08 mm).

Referring still to FIG. 3, a first end portion 70 of the fiber optic cable assembly 60 is shown. The fiber optic cable assembly 60 can include a mating flange 61 positioned at the first end portion 70. The mating flange 61 can define a substantially planar surface extending radially outward from the fiber optic cable assembly 60. The mating flange 61 can be attached to the flange portion 54 such that the fiber optic cable assembly 60 is attached to the probe assembly 30. The mating flange 61 can be attached in any number of ways to the flange portion 54, such as by welding, adhesives, mechanical fasteners, or the like. As such, in one example, the fiber optic cable assembly 60 is attached, such as by being sealingly attached, to the probe assembly 30 and can form a seal with the probe assembly 30. Even further, the first end portion 70 of the fiber optic cable assembly 60 could be attached to the probe assembly 30 in other ways, such as by a threading attachment, mechanical fasteners, or the like. In such an example, the fiber optic cable assembly 60 could be attached to the probe assembly 30 without the mating flange 61 or the flange portion 54.

The fiber optic cable assembly 60 can further include a ferrule 67 positioned at the first end portion 70 of the fiber optic cable assembly 60. As is generally known in the art, the ferrule 67 can provide a termination point for the fiber optic cable assembly 60. The ferrule 67 can include any number of shapes and constructions, and it is to be understood that the ferrule 67 shown in FIG. 3 merely depicts one example ferrule. In this example, the ferrule 67 can include an internal bore 68 through which optical fibers can extend. The ferrule 67 can include a number of materials, such as ceramics, metals, and/or plastics. As such, the ferrule 67 can be provided at the first end portion 70 of the cable assembly and can extend at least partially into the second end portion opening 53.

It is to be understood that the individual fibers of the fiber optic cable assembly 60 are not shown in FIG. 3 for illustrative purposes so as to more clearly depict the internal bore 68 and the second end portion opening 53. However, in a fully assembled state, optical fibers can extend longitudinally within the internal bore 68. As such, the optical fibers can extend through the internal bore 68, through the second end portion opening 53, and at least partially into the internal probe chamber 35.

Figure 4:
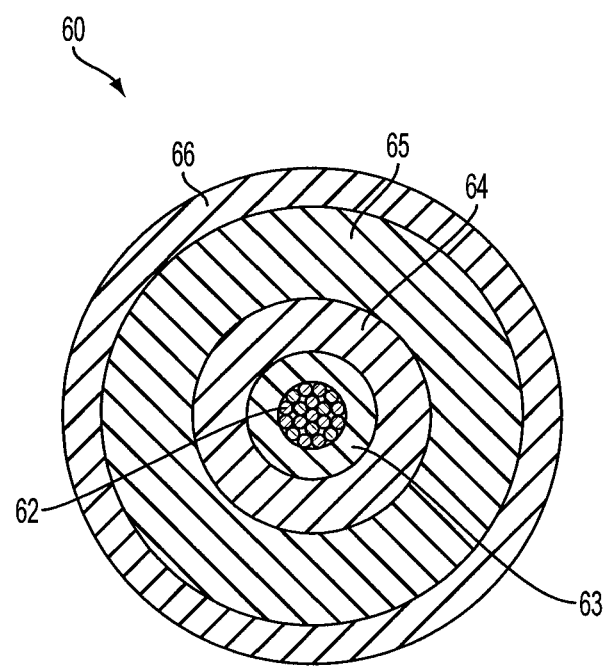
FIG. 4 is a sectional view of an example fiber optic cable assembly along line 4-4 of FIG. 1.

Referring now to FIG. 4, the fiber optic cable assembly 60 can now be described in more detail. FIG. 4 depicts a cross-sectional view along line 4-4 of FIG. 1 of one example of the fiber optic cable assembly 60. While FIG. 4 depicts one example cross-section of the fiber optic cable assembly 60, it is to be understood that the remaining cross-sections of the fiber optic cable assembly 60 could be similar and/or identical to the cross-section shown in FIG. 4. The fiber optic cable assembly 60 can convey the electromagnetic radiation energy indicative of specific characteristics of the flame 8 from the probe assembly 30 to the sensor 80. It is to be understood that by conveying the electromagnetic radiation energy, the fiber optic cable assembly 60 can allow the electromagnetic radiation energy to freely pass from one end of the fiber optic cable assembly 60 to the opposite end. Accordingly, the fiber optic cable assembly 60 can convey the electromagnetic radiation energy by allowing the energy to travel within optical fibers from the probe assembly 30 to the sensor 80.

The fiber optic cable assembly 60 can include a plurality of optical fibers 62 that extend longitudinally between the first end portion 70 and second end portion 72 of the fiber optic cable assembly 60. The fiber optic cable assembly 60 can include any number of optical fibers 62 though, in the shown example, the fiber optic cable assembly 60 includes nineteen optical fibers. Similarly, the size/shape of the optical fibers 62 need not be the same as the size/shape shown in FIG. 4, as the optical fibers 62 could have a larger or smaller diameter. Accordingly, the optical fibers 62 of FIG. 4 are not intended to be limitations upon the present invention.

As is generally known, each of the optical fibers 62 could include a silica core that functions as a light tube that transports the electromagnetic radiation energy along its length between opposing ends. In further examples, the silica core could be surrounded by a cladding material (not shown) that extends coaxially with the silica core between opposing ends. In one example, the cladding material can have a relatively low refractive index and can assist in confining the electromagnetic radiation energy to the silica core. More specifically, electromagnetic radiation energy can reflect off the cladding material and remain within the silica core. The cladding material could be surrounded and/or coated by a buffer material that can protect both the silica core and the cladding material from moisture and/or physical damage. It is to be understood that the optical fibers 62 are not limited to the silica core, cladding material, and buffer material described herein, as this is merely one possible example of the optical fibers 62.

The optical fibers 62 can be surrounded by at least one layer of sock material. In the shown example of FIG. 4, the at least one layer of sock material can include a first sock layer 63 and a second sock layer 64. However, in further examples, the at least one layer of sock material could include more than two sock layers, or as few as one sock layer. The first sock layer 63 and second sock layer 64 can provide protection to the optical fibers 62. The first sock layer 63 and second sock layer 64 can circumferentially surround the cluster of optical fibers 62, with the optical fibers 62 being arranged within a center of a cloth material. As such, the first sock layer 63 and second sock layer 64 can extend coaxially with the cluster of optical fibers 62 between an opposing first end portion 70 and second end portion 72 of the fiber optic cable assembly 60. The first sock layer 63 and second sock layer 64 can include a number of different materials, such as a fiber glass material, or the like.

The fiber optic cable assembly 60 can further include a hose layer 65 that substantially surrounds the optical fibers 62, first sock layer 63, and second sock layer 64. The hose layer 65 can extend substantially coaxially with the optical fibers 62, first sock layer 63, and second sock layer 64 between opposing first end portion 70 and second end portion 72 of the fiber optic cable assembly 60. The hose layer 65 can be formed of a flexible metal-like material, such as stainless steel. The hose layer 65 can provide a protective layer to the fiber optic cable assembly 60, thus protecting the sock layers from damage.

The fiber optic cable assembly 60 can further include an armored braid layer and metal hose 66 that surrounds the optical fibers 62, first sock layer 63, second sock layer 64, and hose layer 65. The armored braid layer and metal hose 66 can have a slightly larger diameter than a diameter of the hose layer 65, such that the armored braid layer and metal hose 66 extends around an outer surface of the hose layer 65. It is to be appreciated that while FIG. 4 depicts the armored braid layer and metal hose 66 as a single layer, the armored braid layer and the metal hose can comprise two separate layers. For example, the armored braid layer can have a slightly larger diameter than the metal hose, such that the armored braid layer extends circumferentially around the metal hose. Along these lines, the metal hose can assist in limiting and/or preventing leakage of fluids, gas, or the like into and out of the fiber optic cable assembly 60.

The armored braid layer and metal hose 66 can include a number of different materials, including stainless steel. It is to be understood that the armored braid is designed to withstand a variety of environments, including relatively high temperature and pressure environments, such that the armored braid layer and metal hose 66 can protect the optical fibers 62. For instance, the armored braid layer and metal hose 66 can be designed to withstand air temperatures, such as in close proximity to the combustion chamber 10, in the range of from about −55° C. (−67° F.) to about 200° C. (392° F.). However, hotter or colder temperatures are also contemplated. Similarly, the armored braid layer and metal hose 66 can be water resistant and can limit or prevent the passage of liquids, moisture, condensation, or the like through the armored braid layer and metal hose 66. As such, the armored braid layer and metal hose 66 can withstand periodic liquid washes that are performed on the turbine compartment 12 with no fluid transport through the armored braid layer and metal hose 66.

Though not shown in the examples, the fiber optic cable assembly 60 can further include one or more support structures, such as cable clamps, that can support the armored braid layer and metal hose 66. The support structures can, in one example, be positioned every 0.91 meters (3 feet) to support the armored braid layer and metal hose 66. For instance, the support structures can be attached to a surface that inside and/or outside the turbine compartment 12, such that the fiber optic cable assembly 60 is sufficiently supported. The fiber optic cable assembly 60 can be readily attached and detached from the support structures, allowing for maintenance, removal, reinstallation, or the like.

The fiber optic cable assembly 60 can be evacuated of gas and/or moisture and included as part of a sealed array. By being included as part of a sealed array, the fiber optic cable assembly 60 can reduce the formation of condensation within the cable assembly and reduce the entrance of gases from an exterior location, such as the combustion chamber 10, into the cable assembly. To seal the fiber optic cable assembly 60, moisture, condensation, and/or gas can first be evacuated from the cable assembly. The moisture, condensation, and/or gas can be removed from the fiber optic cable assembly 60 in any number of ways that are known in the art. For instance, a negative pressure can be applied to one or both of the ends of the cable assembly, such that gases and moisture are evacuated. In the alternative, a purge gas could be supplied to an end of the fiber optic cable assembly 60 to purge the cable assembly from moister, condensation, and/or gas. Once the gases and moisture are evacuated from the fiber optic cable assembly 60, the cable assembly can then be heated to remove at least some of the remaining moisture. Specifically, the fiber optic cable assembly 60 can be heated at a sufficiently high temperature, such that some or all of the remaining moisture in the cable assembly is evaporated. It is to be appreciated that the fiber optic cable assembly 60 can be heated to a variety of different temperatures, depending on factors such as the material used, or the like. In one possible example, the fiber optic cable assembly 60 could be heated to approximately 100° C. (212° F.) to evaporate moisture, though other temperatures are contemplated.

After the gases and moisture have been removed, the fiber optic cable assembly 60 can be filled with an inert gas, such as a dry inert gas. In one example, the inert gas can comprise nitrogen gas, though other gases are contemplated. The inert gas can protect the fiber optic cable assembly 60 from damage due to exposure to air and moisture. For instance, by filling the cable assembly with the inert gas, condensation buildup can be reduced both within the fiber optic cable assembly 60 and at the first end portion 70 adjacent the probe assembly 30. Condensation buildup can cause galvanic corrosion between the hose layer 65 and the second sock layer 64. Furthermore, moisture can damage the silica core of the optical fibers 62 if the moisture were to penetrate the cladding material. In addition, by filling the fiber optic cable assembly 60 with the inert gas, further condensation buildup can be limited when the turbine compartment 12 and combustion chamber 10 are cooled down.

After the fiber optic cable assembly 60 has been filled with the inert gas, the fiber optic cable assembly 60 can further be sealed and included as part of a sealed array. For instance, each of the first end portion 70 and second end portion 72 of the fiber optic cable assembly 60 can be sealed, such that undesirable materials are limited and/or prevented from entering an interior of the fiber optic cable assembly 60. The undesirable materials can include, but are not limited to, moisture, condensation, gas from the probe assembly 30, or the like. To seal the first end portion 70 and second end portion 72, a sealant material can be deposited at both of the first end portion 70 and the second end portion 72. The sealant material can substantially surround the optical fibers 62 and fill in some or all of the gaps between the optical fibers 62. The sealant material can form a bond with the outer surface of the buffer material and with an inner surface of the cloth material. In one example, the sealant material can include a ceramic silicone sealant, however a number of different sealant materials are contemplated. The sealant material can, in one example, be chosen to withstand a temperature in the range of about 380° C. (716° F.). As such, once the fiber optic cable assembly 60 has been sealed, undesirable materials are limited from entering the cable assembly while the inert gas is contained within the cable assembly.

Figure 5:
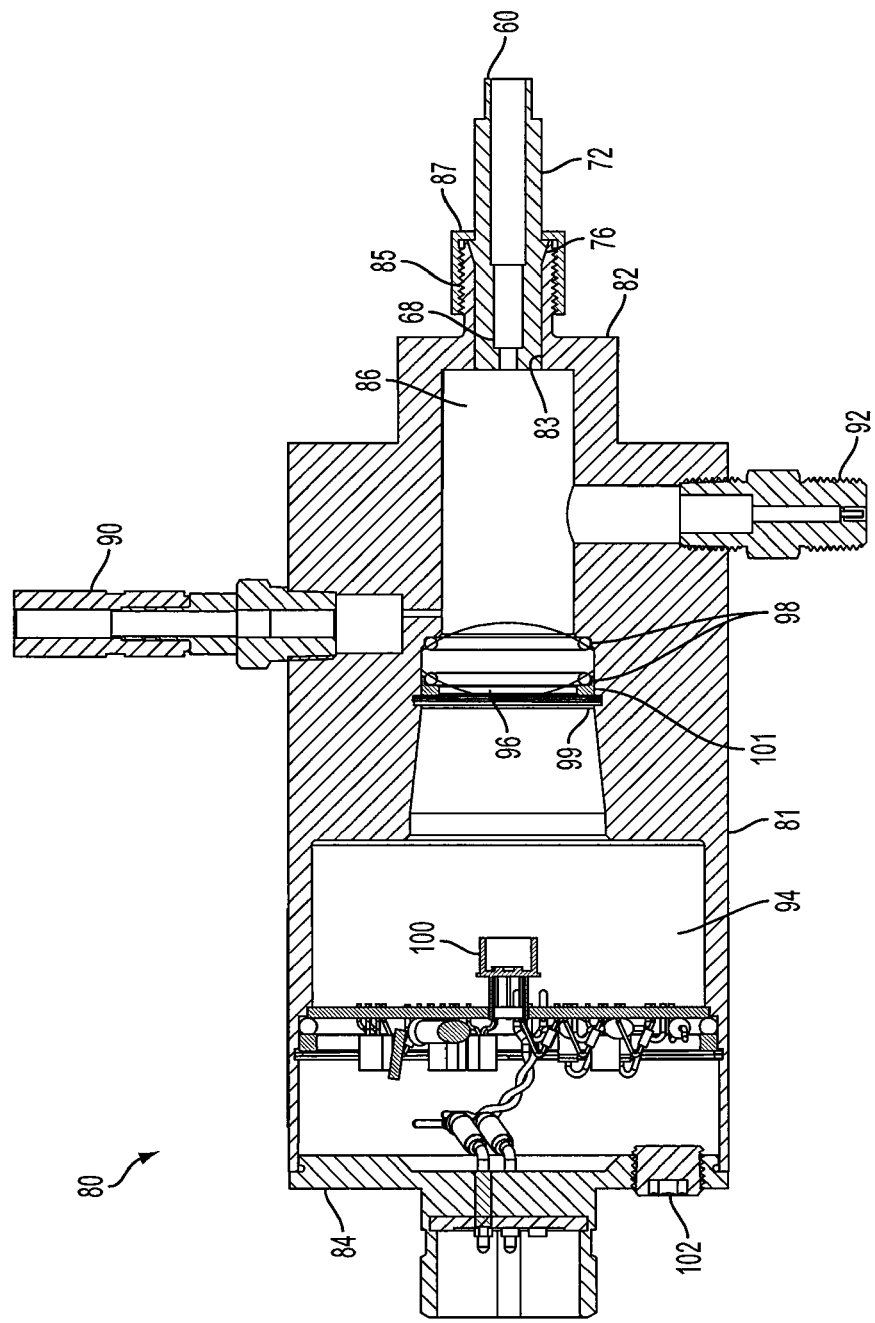
FIG. 5 is a sectional view of an example sensor along line 5-5 of FIG. 1.

Referring now to FIG. 5, a cross-sectional view along line 5-5 of FIG. 1 is shown, depicting an example of the sensor 80. A first end portion 82 of the sensor 80 can be attached to the second end portion 72 of the fiber optic cable assembly 60. The first end portion 82 can include a sensor opening 83 through which the second end portion 72 of the fiber optic cable assembly 60 can extend. As shown, the fiber optic cable assembly 60 can also include an end cap 87. The end cap 87 can include an internal bore extending longitudinally through the end cap 87, and can include an internal threaded portion.

The fiber optic cable assembly 60 can be attached to the sensor 80 in any number of ways. For instance, in the shown example, the sensor 80 can include a threaded projection 85 that engages with the end cap 87 of the fiber optic cable assembly 60. In operation, the fiber optic cable assembly 60 can pass through the end cap 87. The end cap 87 can be attached in a threaded manner to the threaded projection 85. As such, a projection 76 of the fiber optic cable assembly can be positioned between the threaded projection 85 on one side and the end cap 87 on a second side. Accordingly, the fiber optic cable assembly 60 can be removably attached to the sensor 80.

It is to be understood that any number of attachment structures are contemplated for attaching the fiber optic cable assembly 60 to the sensor 80, and the example of FIG. 5 merely depicts one possible example. For instance, the fiber optic cable assembly 60 could be attached by a variety of mechanical fasteners, such that the end cap and threaded projection may not be provided. Mechanical fasteners could include, but are not limited to, a nut and fastener type attachment, a screw and threading type attachment, or the like. In other examples, the fiber optic cable assembly 60 could be attached by a similar or identical welding attachment depicted in FIG. 3 (attachment of first end portion 70 of fiber optic cable assembly 60 to the probe assembly 30). Even further, the fiber optic cable assembly 60 could be attached to the sensor 80 with one or more adhesives. Accordingly, the attachment of the fiber optic cable assembly 60 to the sensor 80 in FIG. 5 includes only one possible example, though a number of attachment means are envisioned.

It is to be understood that the optical fibers 62 of the fiber optic cable assembly 60 are not shown in FIG. 5 for illustrative purposes so as to more clearly depict the internal bore 68 and the sensor opening 83. However, in a fully assembled state, the optical fibers 62 can extend longitudinally within the internal bore 68. As such, the optical fibers 62 can extend through the internal bore 68, through the sensor opening 83, and at least partially into the sensor 80.

Referring still to FIG. 5, the structure of the sensor 80 can now be described in more detail. It is to be understood that the sensor 80 is somewhat generically shown, and is not limited to the example shown in FIG. 5. Accordingly, the sensor 80 can include a number of different sizes and configurations while still retaining the function described herein.

The sensor 80 can be positioned outside of the turbine compartment 12 and spaced a distance apart from the combustion chamber 10. Accordingly, the sensor 80 can be positioned in a location that has a lower temperature than within the turbine compartment 12, such that electronics can be used in the sensor 80 without being subjected to relatively high temperatures.

The sensor 80 can include a sensor body 81 extending between the first end portion 82 and opposing second end portion 84. The sensor body 81 can include a substantially hollow internal bore extending between the first end portion 82 and the second end portion 84. The sensor body 81 can be formed from a number of different materials, including a variety of metal-like materials that can be resistant to corrosion. For instance, the sensor body 81 can include 304 stainless steel, 316 stainless steel, or the like.

The sensor 80 can include a first sensor chamber 86 positioned adjacent the first end portion 82 of the sensor body 81. The first sensor chamber 86 can be bound by the first end portion 82, internal walls of the sensor body 81, and a sensor lens 96. The first sensor chamber 86 can define a substantially cylindrically shaped structure extending along the longitudinal axis of the sensor body 81. The first sensor chamber 86 can be sealed during installation, with the chamber being purged of gas, moisture, condensation, or the like. A number of devices can be used to seal the first sensor chamber 86. For instance, though not limited to this example, the first sensor chamber 86 can include one or more valve assemblies that function to remove gas, moisture, condensation, or the like.

In the example shown in FIG. 5, the one or more valve assemblies can include a low pressure valve 90 and a discharge valve 92. Together, the low pressure valve 90 and discharge valve 92 can function to purge the contents of the first sensor chamber 86. The low pressure valve 90 and discharge valve 92 can each be placed in fluid communication with the first sensor chamber 86. Openings, apertures, or the like can extend radially through the sensor body 81 from the first sensor chamber 86 to an outer wall of the sensor body 81. The low pressure valve 90 and discharge valve 92 can each be in fluid communication with one of the openings, such that a gas flow path is formed from each of the low pressure valve 90 and discharge valve 92, through the sensor body 81, and into the first sensor chamber 86.

Together, the low pressure valve 90 and discharge valve 92 can purge the contents of the first sensor chamber 86. Specifically, the low pressure valve 90 can be operatively attached to a gas supply, such that gas can be supplied to the first sensor chamber 86 through the low pressure valve 90. The gas can include a variety of gases that function to purge the sensor chamber, and, in one possible example, can include a dry inert gas such as nitrogen. The gas can be pumped through the low pressure valve 90. As the supply gas builds up in the first sensor chamber 86, the contents of the first sensor chamber 86 can be evacuated and exit through the discharge valve 92. The contents can include moisture, condensation, or the like. Accordingly, the contents of the first sensor chamber 86 can exit through the discharge valve 92, such that the supply gas can function to remove moisture, condensation, or the like that is present in the first sensor chamber 86. Accordingly, the low pressure valve 90 and discharge valve 92 can perform a purge of the first sensor chamber to remove moisture.

It is to be understood that the valve assemblies, including the low pressure valve 90 and discharge valve 92, shown in FIG. 5 depict merely one possible example of purging the contents of the first sensor chamber 86. Further valve assembly designs are contemplated, such that the sensor 80 is not limited to the example shown in FIG. 5. For instance, in other examples, the first sensor chamber 86 could merely include one or more openings that can receive supply gas from a gas supply. Accordingly, the valve assemblies shown in FIG. 5 include only one possible example of removing/purging the contents of the first sensor chamber 86, as a number of different structures and methods for performing the same function are envisioned.

The sensor 80 can further include a second sensor chamber 94 positioned downstream from the first sensor chamber 86. The second sensor chamber 94 can be positioned within the internal bore of the sensor body 81 and can be positioned between the first sensor chamber 86 and the second end portion 84. The second sensor chamber 94 can be separated from the first sensor chamber 86 by the sensor lens 96. The second sensor chamber 94 can be sealed and backfilled with a gas, including a dry inert gas such as argon. By backfilling the second sensor chamber 94 with the gas, the second sensor chamber 94 can limit and reduce the entrance of moisture, condensation, or the like.

The second sensor chamber 94 can, in one example, be provided with a purge opening 102. The purge opening 102 can assist in backfilling the second sensor chamber 94 with the gas. The purge opening 102 is shown to be positioned at the second end portion 84 of the sensor body 81, though the purge opening 102 is not limited to such a location. Rather, the purge opening 102 could be positioned laterally on a side of the sensor body 81, closer to the first end portion 82, or the like. In operation, the purge opening 102 can be in fluid communication with a gas supply that can supply the dry inert gas. Once the dry inert gas has been supplied through the purge opening 102 and into the second sensor chamber 94, the purge opening 102 can be closed and sealed. In the shown example of FIG. 5, the purge opening 102 can be sealed by means of a threaded insert structure, though a number of sealing structures are envisioned. As such, the sensor 80 is not limited to the purge opening 102 in the shown example.

The sensor 80 can further include the sensor lens 96 positioned within the internal bore separating the first sensor chamber 86 and the second sensor chamber 94. The sensor lens 96 can be positioned downstream from the first end portion 82 of the sensor body 81. As will be described in more detail below, the sensor lens 96 can receive and focus the electromagnetic radiation energy from the fiber optic cable assembly 60. The sensor lens 96 can be can be oriented substantially perpendicularly with respect to the longitudinal axis of the sensor body 81, such that the sensor lens 96 extends across the internal bore. The sensor lens 96 can include a number of different types of lenses, such as a biconvex lens, plano-convex lens, or the like. Furthermore, the sensor lens 96 can include a fused silica lens, in one example.

The sensor lens 96 can be supported by one or more O-rings 98. The shown example of FIG. 5 includes two O-rings, however, it is to be understood, more or fewer O-rings are envisioned. The O-rings 98 can be positioned on opposing sides of the sensor lens 96, such that the sensor lens 96 is substantially sandwiched between the O-rings 98. The O-rings 98 can include a circularly shaped structure having a bore extending through a center. The O-rings 98 can be formed of a number of different materials, including elastomer materials, Viton, or the like. The O-rings 98 can sandwich the sensor lens 96 such that one of the O-rings 98 is positioned upstream and adjacent the sensor lens 96 while the second O-ring is positioned downstream and adjacent the sensor lens 96. The O-rings 98 can, in one example, be attached to either or both of the sensor body 81 and sensor lens 96, such that the sensor lens 96 can be limited from moving axially along the length of the sensor body 81. Moreover, the O-rings 98 can form a substantially air-tight seal between the sensor lens 96 and the sensor body 81, such that gas, air, liquids, or the like are limited and/or prevented from passing around the sensor lens 96 from the first sensor chamber 86 to the second sensor chamber 94, and vice versa.

The sensor 80 can further include a washer compression ring 101 positioned adjacent and downstream from the O-rings 98. The washer compression ring 101 can extend circumferentially around an internal bore of the sensor 80. The washer compression ring 101 can include a deformable material that can compress in response to a force. For example, the washer compression ring 101 can include any number of elastomer-like materials. The washer compression ring 101 can contact the O-rings 98 such that the washer compression ring 101 can limit and/or prevent axial movement of the O-rings 98 and the sensor lens 96.

The sensor 80 can further include a retaining ring 99. The retaining ring 99. The retaining ring 99 can be similar or identical to the retaining ring 51 in the probe assembly 30. The retaining ring 99 in the sensor 80 can be received within an indentation, groove, or the like formed within an interior surface of the sensor body 81. The retaining ring 51 can provide further support for the sensor lens 96, O-rings 98, and washer compression ring 101, and can limit and/or prevent axial movement of these structures. The retaining ring 99 is positioned downstream and adjacent the washer compression ring 101. Of course, it is to be appreciated that the retaining ring 99 includes merely one possible example of a retaining ring, as any number of structures that can limit axial movement of the sensor lens 96 are contemplated.

The sensor 80 can further include a photodiode 100 positioned downstream from the sensor lens 96. The photodiode 100 can include a solid state ultraviolet sensor that receives the focused electromagnetic radiation energy from the fiber optic cable assembly 60 through the sensor lens 96. The photodiode 100 can be square shaped and is about 1.4 millimeters long diagonally. In one example, the sensor lens 96 can focus light, including the electromagnetic radiation energy, onto a spot on the photodiode 100 that is about 1.7 millimeters+/−0.08 millimeters in diameter. Of course, it is understood that a variety of photodiodes can be used in the sensor 80, such that the photodiode 100 is not limited to the aforementioned dimensions. In one example, the photodiode 100 can include a silicon carbide photodiode.

The photodiode 100 can receive the electromagnetic radiation energy and can generate a current output signal, such as a photocurrent, based on the electromagnetic radiation energy. As is generally known, the electromagnetic radiation energy can include ultraviolet (UV) radiation that has a wavelength in a range from about 10 nm to about 400 nm. The photodiode 100 can generate a photocurrent that is converted to a current that is proportional to the intensity level of the UV radiation received within a specific spectral bandwidth. For instance, the photodiode 100, including the silicon carbide photodiode, can have a spectral response in a range of from about 190 nanometers (nm) to about 400 nm. As such, the photodiode 100 has a relatively broad spectral response that covers a 310 nm peak of the flame 8, thus allowing for a relatively reliable detection of the 310 nm emission of the flame 8. By having a high end spectral response cutoff (400 nm in this example), the photodiode 100 can therefore be "blind" to potential interfering blackbody radiation from the walls of the combustion chamber 10.

As is generally known, the photodiode 100 can be included as part of an amplifier circuit. The amplifier circuit is shown somewhat generically in FIG. 5, and could include any number of configurations not limited to FIG. 5. The photodiode 100 can generate a photocurrent that is proportional to the ultraviolet light intensity to which the photodiode 100 is exposed. The photocurrent from the photodiode 100 can be processed and amplified by signal circuitry to produce an electrical signal. For instance, in one example, the photodiode 100 can convert electromagnetic radiation energy to an electrical signal in the form of a photocurrent. As is generally known, the photocurrent may be amplified, such that after amplification, the photocurrent is converted into a current in the range of about 4 milliamperes (mA) to about 20 milliamperes.

This electrical signal in the form of a current can be indicative of the specific characteristics of the flame 8. The specific characteristics of the flame 8 can include, for example, the presence or absence of the flame 8 within the combustion chamber 10. For instance, in the event of a flame-out condition wherein the flame 8 has been extinguished, the absence of electromagnetic radiation energy at the photodiode 100 will be detected. This absence of electromagnetic radiation energy can cause the photodiode 100 to provide an electrical signal in the form of a photocurrent that is low or zero. In one example, this electrical signal can be sent to a fuel control apparatus, or the like, that can reduce and/or stop the supply of fuel through the fuel nozzle 13 and into the combustion chamber 10. As such, the electrical signal from the photodiode 100 can be used to control the supply of fuel into the fuel nozzle 13.

Referring now to FIG. 1, the flame sensor apparatus 6 operation can now be described in more detail. Fuel can be provided to the combustion chamber 10 through the fuel nozzle 13, producing the flame 8. A sight tube 15 can project a distance outwardly from the combustion chamber 10 and can define an optical path from the sight tube 15 towards the flame 8. The probe assembly 30 can be attached to the sight tube, such that the probe assembly 30 is spaced a distance away from the combustion chamber 10. Electromagnetic radiation energy, indicative of the specific characteristics of the flame 8, is conveyed from the flame 8 in the combustion chamber 10, through the sight tube 15 and into the probe assembly 30. Once in the probe assembly 30, the electromagnetic radiation energy can be focused by the probe lens 42 (shown in FIG. 3) onto optical fibers 62 at the first end portion 70 of the fiber optic cable assembly 60. The fiber optic cable assembly 60 can extend between the first end portion 70, which is positioned within the turbine compartment 12 to the second end portion 72, which is positioned outside of the turbine compartment 12. The electromagnetic radiation energy can travel along the length of the fiber optic cable assembly 60 from the first end portion 70 to the opposing second end portion 72.

Referring now to FIG. 5, the electromagnetic radiation energy at the second end of the fiber optic cable assembly 60 can enter the sensor 80. The sensor 80 is positioned a distance away from the combustion chamber 10 outside of the turbine compartment 12, such that the sensor 80 is not located within the relatively high temperature/vibration environment of the turbine compartment 12. The electromagnetic radiation energy can be focused by the sensor lens 96 onto the photodiode 100. In response, the photodiode 100 can produce an electrical signal based on the intensity of the electromagnetic radiation energy. This electrical signal can be in the form of a current output that is indicative of the specific characteristics of the flame 8, including, but not limited to, the presence or absence of the flame. Accordingly, in the absence of the flame 8, the current output can be low or zero. This low current output can trigger a shut off of the fuel being provided to the combustion chamber 10. By shutting off the fuel supply to the combustion chamber 10, the likelihood of damage to the turbine can be reduced. Moreover, by positioning the sensor 80 at a location outside of the turbine compartment 12, temperature sensitive electronic components in the sensor 80 can safely and reliably operate.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. A flame sensor apparatus comprising:
   a sensor to determine specific characteristics of a flame within a combustion chamber, the sensor including a silicon carbide photodiode, a sealed internal sensor chamber filled with an inert gas and at least one valve assembly in fluid communication with the internal sensor chamber for supplying the inert gas to the internal sensor chamber, wherein the sensor is spaced a distance from the combustion chamber; and
   a fiber optic cable assembly extending between the sensor and the combustion chamber, the fiber optic cable assembly being attached to the sensor with the fiber optic cable assembly being in fluid communication with the internal sensor chamber through an internal bore, the fiber optic assembly comprising optical fibers and at least one layer within which the optical fibers are located, the fiber optic cable assembly being configured to convey the specific characteristics of the flame from the combustion chamber to the sensor, wherein the fiber optic cable assembly is included as part of a sealed array with the internal sensor chamber filled with the inert gas supplied by the at least one valve assembly, with the inert gas located within the fiber optic cable assembly and outside of the optical fibers.

2. The flame sensor apparatus of claim 1, wherein the specific characteristics of the flame include the presence and absence of the flame within the combustion chamber.

3. The flame sensor apparatus of claim 1, wherein the silicon carbide photodiode is configured to trigger a shut off of fuel to the combustion chamber.

4. The flame sensor apparatus of claim 1, wherein the fiber optic cable assembly is sealed at opposing ends and filled with nitrogen gas.

5. The flame sensor apparatus of claim 1, wherein the fiber optic cable assembly is attached to a first end portion of the sensor, the sensor further including a lens positioned at the internal sensor chamber of the sensor between the first end portion and the silicon carbide photodiode, the lens being configured to focus electromagnetic radiation energy from the fiber optic cable assembly onto the silicon carbide photodiode.

6. The flame sensor apparatus of claim 5, wherein the internal sensor chamber of the sensor is a first sensor chamber positioned between the first end portion of the sensor and the lens and the sensor includes a second sensor chamber positioned between the lens and an opposing second end of the sensor, the silicon carbide photodiode being positioned in the second sensor chamber.

7. The flame sensor apparatus of claim 6, wherein the silicon carbide photodiode is configured to convert electromagnetic radiation energy from the fiber optic cable assembly to an electrical signal in the form of a current output in the range of about 4 milliamperes to about 20 milliamperes, the current output being indicative of the specific characteristics of the flame.

8. The flame sensor apparatus of claim 6, wherein the second sensor chamber is sealed and filled with the inert gas.

9. The flame sensor apparatus of claim 1, further including a sight tube projecting from the combustion chamber and defining an optical path from the flame and through the sight tube.

10. The flame sensor apparatus of claim 9, further including a probe assembly attached to the sight tube at a first end portion of the probe assembly and configured to receive specific characteristics of the flame from the sight tube, the probe assembly comprising:
    an internal probe chamber extending between the first end portion and an opposing second end portion of the probe assembly with the fiber optic cable assembly sealingly attached to the second end of the probe assembly;
    a sapphire window disposed within the internal probe chamber, the sapphire window being sealed within the internal probe chamber and configured to provide a pressure barrier; and
    a lens disposed within the internal probe chamber between the sapphire window and the second end, the lens being supported by at least one metal washer such that the lens is configured to focus light from the sight tube onto an end of the fiber optic cable assembly.

11. The flame sensor apparatus of claim 10, wherein the lens is configured to focus electromagnetic radiation energy from the flame onto the fiber optic cable assembly.

12. The flame sensor apparatus of claim 1, wherein the at least one valve assembly of the sensor includes two separate valves connected to the internal sensor chamber, a first of the two valves is a discharge valve to remove unwanted contents prior to providing the gas and a second of the two valves is a valve to supply the inert gas.

13. A flame sensor apparatus comprising:
    a sensor for sensing specific characteristics of a flame within a combustion chamber, the sensor including a silicon carbide photodiode, a sealed internal chamber filled with an inert gas and at least one valve assembly in fluid communication with the internal chamber for supplying the inert gas to the internal chamber;
    a probe assembly spaced a distance away from the combustion chamber, the probe assembly configured to receive specific characteristics of the flame from the combustion chamber; and
    a fiber optic cable assembly extending between the sensor and the probe assembly, the fiber optic cable assembly being attached to the sensor with the fiber optic cable assembly being in fluid communication with the internal chamber through an internal bore, the fiber optic assembly comprising optical fibers and at least one layer within which the optical fibers are located, the fiber optic cable assembly being configured to convey the specific characteristics of the flame from the probe assembly to the sensor, wherein the fiber optic cable assembly is included as part of a sealed array with the internal chamber filled with the inert gas supplied by the at least one valve assembly, with the inert gas located within the fiber optic cable assembly and outside of the optical fibers.

14. The flame sensor apparatus of claim 13, further including a sight tube projecting from an exterior of the combustion chamber, the sight tube defining an optical path through the sight tube and towards the flame.

15. The flame sensor apparatus of claim 14, wherein the probe assembly is attached to an end of the sight tube opposite from the combustion chamber, the probe assembly being configured to receive the specific characteristics of the flame from the sight tube.

16. The flame sensor apparatus of claim 13, wherein the probe assembly comprises:
   an internal probe chamber extending between a first end portion and an opposing second end of the probe assembly, the fiber optic cable assembly sealingly attached to the internal probe chamber at the second end of the probe assembly through an internal bore;
   a sapphire window disposed within the internal chamber, the sapphire window configured to form a seal with the internal probe chamber and provide a pressure barrier; and
   a lens disposed within the internal probe chamber between the sapphire window and the second end, the lens being supported by at least one metal washer such that the lens is configured to focus light from the sight tube onto an end of the fiber optic cable assembly.

17. A method of sensing specific characteristics of a flame within a combustion chamber, comprising the steps of:
   providing a fiber optic cable assembly;
   providing a sensor having a silicon carbide photodiode therein;
   receiving electromagnetic radiation energy from the flame by the fiber optic cable assembly;
   conveying the electromagnetic radiation energy from the fiber optic cable assembly to the sensor spaced a distance away from the combustion chamber;
   focusing the electromagnetic radiation energy from the fiber optic cable assembly onto the silicon carbide photodiode within the sensor; and
   sensing the specific characteristics of the flame with the silicon carbide photodiode based on the electromagnetic radiation energy;
   wherein the steps of providing a fiber optic cable assembly and providing a sensor includes providing the fiber optic cable assembly with: optical fibers, at least one layer within which the optical fibers are located and an inert gas, with the inert gas located within the fiber optic cable assembly and outside of the optical fibers, providing the sensor with: a sealed internal sensor chamber, the inert gas located within the internal sensor chamber and at least one valve assembly that is in fluid communication within the internal sensor chamber, and supplying the inert gas to the internal sensor chamber and the fiber optic cable assembly by the at least one valve assembly.

18. The method of claim 17, further including the step of removing moisture from the fiber optic cable assembly comprising the steps of:
   removing gases from an interior of the fiber optic cable assembly by the at least one valve assembly; and
   heating the fiber optic cable assembly at a sufficiently high temperature to remove moisture.

19. The method of claim 18, wherein the step of providing the sensor with at least one valve assembly includes providing the sensor with two separate valves connected to the internal sensor chamber, a first of the two valves is a discharge valve to remove unwanted contents prior to providing the gas and a second of the two valves is a valve to supply the inert gas.

20. The method of claim 17, further including the step of converting the electromagnetic radiation energy to an electrical signal in the form of a current output in a range of about 4 milliamperes to about 20 milliamperes, the current output being indicative of the specific characteristics of the flame.

* * * * *